United States Patent [19]

Martin

[11] Patent Number: 4,976,687
[45] Date of Patent: Dec. 11, 1990

[54] APPARATUS FOR CONTROLLING THE SUPPLYING OF INTRAVENOUS FLUIDS

[76] Inventor: James Martin, 8322 County Line Rd., Burr Ridge, Ill. 60521

[21] Appl. No.: 201,760

[22] Filed: Jun. 3, 1988

Related U.S. Application Data

[63] Continuation-in-part of Ser. No. 48,234, May 11, 1987, abandoned.

[51] Int. Cl.⁵ ............................................. A61M 5/172
[52] U.S. Cl. ................................ 604/65; 128/DIG. 13; 604/118; 604/207; 604/236; 604/246
[58] Field of Search ................. 604/31, 65-67, 604/118, 207, 236, 246-247, 250; 128/DIG. 12, DIG. 13

[56] References Cited

U.S. PATENT DOCUMENTS

| | | | |
|---|---|---|---|
| 3,323,550 | 6/1967 | Lee | 137/809 X |
| 4,187,847 | 2/1980 | Loeser | 128/DIG. 12 |
| 4,207,871 | 6/1980 | Jenkins | 604/246 X |
| 4,340,050 | 7/1982 | Noiles | 604/246 |
| 4,447,230 | 5/1984 | Gula et al. | 604/247 X |
| 4,496,351 | 1/1985 | Hillel et al. | 604/250 |
| 4,515,588 | 5/1985 | Amendolia | 604/247 X |
| 4,540,027 | 9/1985 | Forberg | 604/247 X |
| 4,613,325 | 9/1986 | Abrams | 604/65 |
| 4,617,014 | 10/1986 | Cannon et al. | 604/67 |
| 4,778,450 | 10/1988 | Kamen | 604/65 |

*Primary Examiner*—William E. Kamm
*Attorney, Agent, or Firm*—Edmond T. Patnaude

[57] ABSTRACT

Intravenous fluid is supplied under the control of a microprocessor from a reservoir to a cannula through a flow member and a flow control device which responds, via the microprocessor, to the line pressures upstream and downstream of the control device. First and second transducers and first and second check valves are connected respectively upstream and downstream of the control device, and a constant flow resistance device is connected in series with the flow-control device to enhance the accuracy of the system.

7 Claims, 5 Drawing Sheets

APPARATUS FOR CONTROLLING THE SUPPLYING OF INTRAVENOUS FLUIDS

This application is a continuation-in-part of copending application Ser. No. 048,234 filed by me on May 11, 1987, now abandoned.

The present invention relates in general to the feeding of intravenous fluids to patients, and it relates in particular to a new and improved method and apparatus for maintaining the rate of flow of the I.V. fluid to the patient at a preset rate irrespective of changes in the pressure of the fluid.

BACKGROUND OF THE INVENTION

Intravenous fluids are generally supplied to the patient under the force of gravity by positioning a reservoir containing an I.V. liquid reservoir at atmospheric pressure at an elevated position relative to the patient. The rate of flow is set by a manually adjustable valve connected in the line between the reservoir and the patient, and once set, the rate remains essentially constant as long as the head of liquid does not change appreciably. Of course, as the liquid is being fed to the patient the pressure head slowly decreases causing the flow rate to decrease proportionately, and if a precise amount of liquid is to be supplied to the patient this change must be taken into account when the valve is initially set or in the alternative the manual valve can be reset from time to time. However, should the patient roll over or make some other movement which appreciably changes the vertical distance between the reservoir and the cannula the flow rate changes more dramatically.

It would be desirable to provide an I.V. system wherein the I.V. fluid reservoir is pressurized and wherein the fluid is supplied to the patient at a substantially precise preset rate irrespective of changes in the pressure head of fluid above the patient. It would also be desirable to include in such a system means for interrupting the supply of I.V. fluid once a preset volume of fluid has been administered to the patient, and to provide an alarm responsive to changes in the pressure feed rate and volume for attracting a nurse or physician when they are needed.

SUMMARY OF THE INVENTION

Briefly, there is provided in accordance with one embodiment of the present invention an I.V. system which includes a pressurized supply of I.V. fluid having an adjustable flow rate control valve connected over the outlet port thereof and having its outlet connected to a flow meter by means of flexible tubing. The outlet of the flow meter is connected by a flexible tubing to a cannula which includes a hollow needle for insertion into the body of a patient.

A separate control box includes a servo motor and a motor driven cam which is adapted to receive a short length of the flexible tubing and thus to function as a control valve by controllably varying the size of the opening through the tubing thereby to control the flow rate. The control box further includes a first sensor which is responsive to the output signal from the flow meter and a second sensor which is responsive to the pressure in the tubing downstream of the control valve. A microprocessor mounted in the control box responds to the signals from the flow meter and the pressure sensor to controllably position the motor and the cam and in turn the flow rate through the tubing.

In another embodiment there is provided a flow control valve in the line between the reservoir and the patient, and a pressure transducer is provided in the line upstream of the control valve for producing a signal proportional to the fluid pressure in the reservoir. A microprocessor responds to the output signal from the pressure transducer and to a manual rate set to adjust the operation of the flow control valve to maintain the set flow rate irrespective of changes in pressure and viscosity. In a preferred embodiment a flow resistor is connected between the pressure transducer and the flow control valve to provide a predetermined time delay and thereby permit extremely precise control of the flow rate.

In still another embodiment, a second pressure transducer is connected to the line downstream of the flow control valve, and its output signal is inputted to the microprocessor. Inasmuch as the flow rate through the control valve is dependent on the pressure differential the use of a pre-valve transducer and a post-valve transducer enables the computer to precisely control the flow rate through the valve. Should the pressure at the post-valve transducer exceed the pressure at the pre-valve transducer the microprocessor activates an alarm. Where the reservoir is not pressurized and the flow rate is dependent on gravity alone, this condition will occur when the reservoir is lower than the patient because, for example, the reservoir has fallen from its hanger or the patient has gotten out of bed. Where desired, a pump may be connected in the system and controlled by the computer to maintain the preset flow rate if the pressure differential across the control valve falls below a predetermined value.

In those systems where a drip chamber is not used, the post-valve transducer may be used in conjunction with the microprocessor to controllably adjust the flow control valve to maintain the preset flow rate.

GENERAL DESCRIPTION OF THE DRAWINGS

Further objects and advantages and a better understanding of the present invention will be had by reference to the following detailed description taken in connection with the accompanying drawings wherein.

DETAILED DESCRIPTION OF THE PREFERRED EMBODIMENTS

Figure 1:
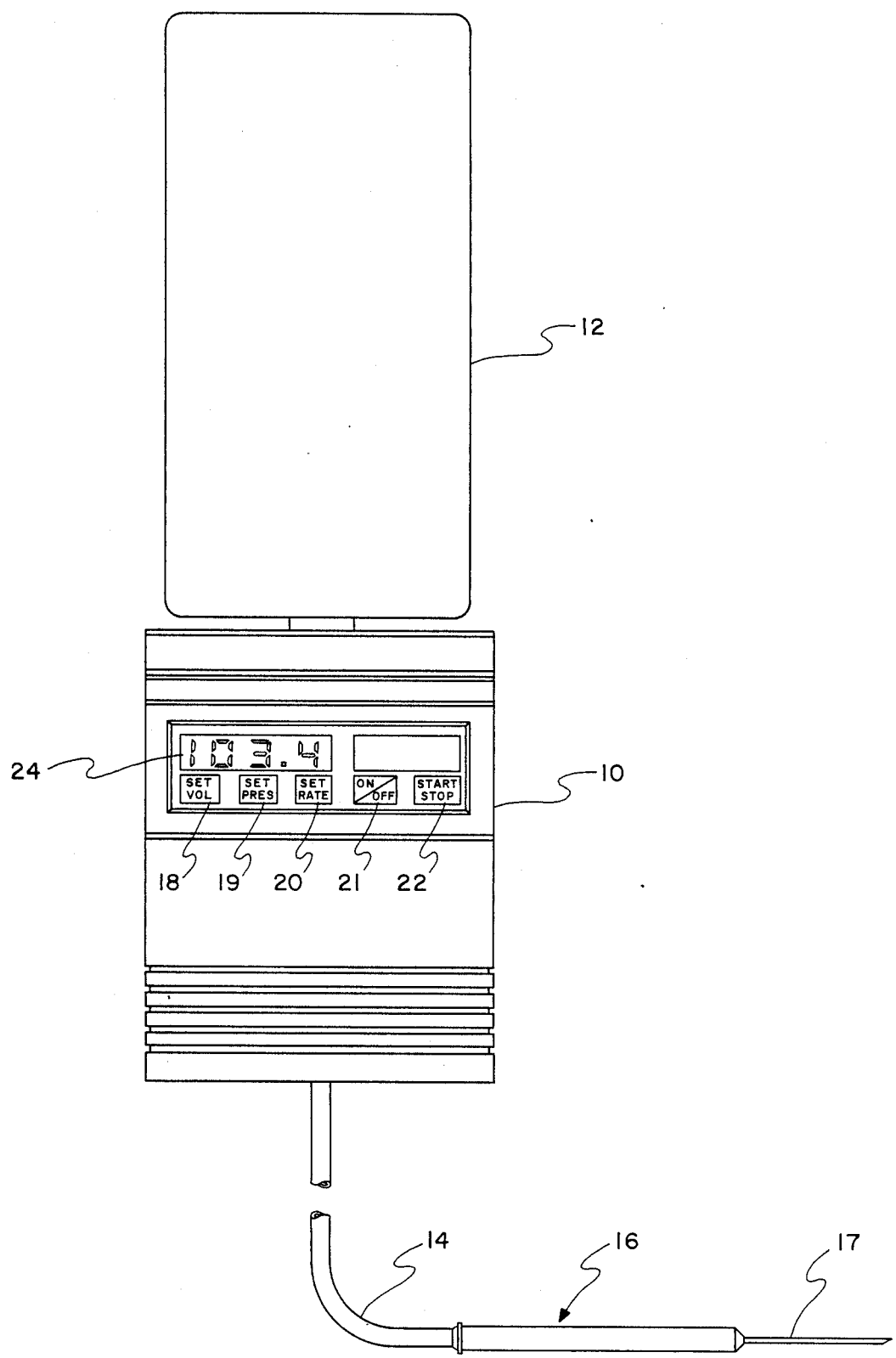
FIG. 1 is a front elevational view of an intravenous feeding system embodying the present invention.

Referring to FIG. 1 it may be seen that a pressurized intravenous feeding system comprises a control box 10 to the top of which is mounted an I.V. fluid container 12 and from the bottom of which extends a flexible tube 14 to which a conventional cannula 16 including a tubular I.V. needle 17 is connected. The control box 10 is provided on its front face with a plurality of depressible control buttons 18, 19, 20, 21 and 22 and a digital display 24. As is more fully described hereinafter in connection with FIG. 6, after the container 12 has been fitted into the control box 10 and the button 21 depressed to turn the system on, the operator depresses the button 18 to enter into a microprocessor (not shown) the volume of fluid to be administered to the patient, that volume being shown on the display 24. The operator then presses the button 19 to enter into the microprocessor the maximum pressure at which the fluid is to be administered to the patient, and the operator then presses the button 20 to set the flow rate at which the fluid is to be administered, that rate being then shown on the display 24.

The button 22 is then momentarily depressed to fill the feed tube and needle with I.V. fluid and the needle 17 is then inserted into a vein or other part of the patient and the button 22 is again depressed to start the flow of fluid at the set rate. When the preset volume has been fed to the patient the flow of fluid to the needle is interrupted and preferably an alarm is actuated. The alarm may be visual, audible or both. Should the needle become blocked, thereby increasing the pressure in the tube 14, the flow will also be interrupted and the alarm will be actuated.

Considered in greater detail and with reference to FIGS. 2–5, the control box 10 includes a front cover 26 hingedly connected to the box 10. The container 12 includes a rigid, generally cylindrical housing in which is disposed an elastomeric reservoir 30 containing I.V. fluid under pressure. An on/off valve 32 is mounted over the outlet at the bottom of the reservoir and includes a rotatable cap 34 which is adapted to be rotated through ninety degrees between the fully open and the fully closed position.

A flexible tube 36 is connected at its upper end to the outlet port 38 of the valve 32 and is connected at its lower end to a transducer 40 which operates in conjunction with other elements mounted in the control box 10 to sense the rate of flow of fluid through the transducer and to sense the pressure of fluid in the transducer 40. The tube 14 which connects to the cannula is connected to the outlet at the bottom of the transducer 40.

Figure 3:
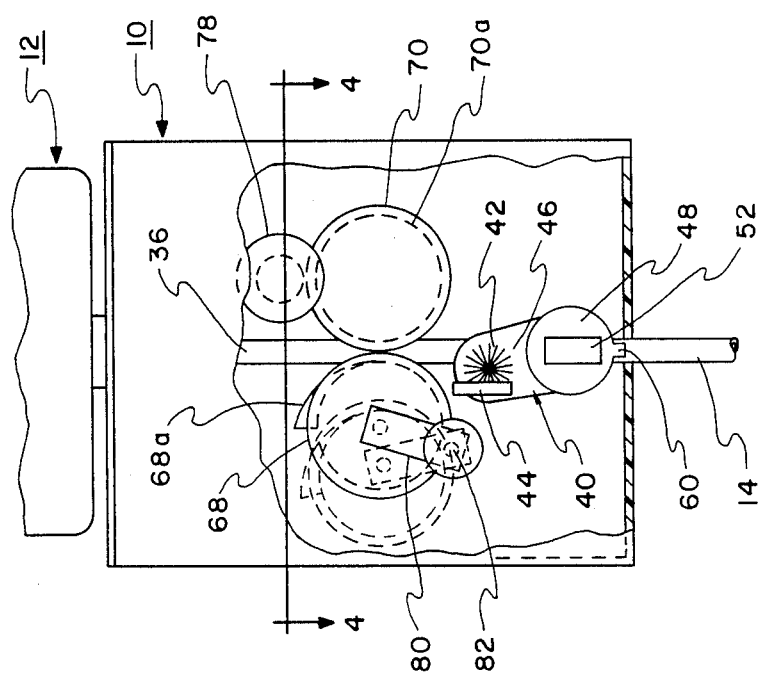
FIG. 3 is a partially sectioned view taken along the line 3—3 in FIG. 2.
Figure 5:
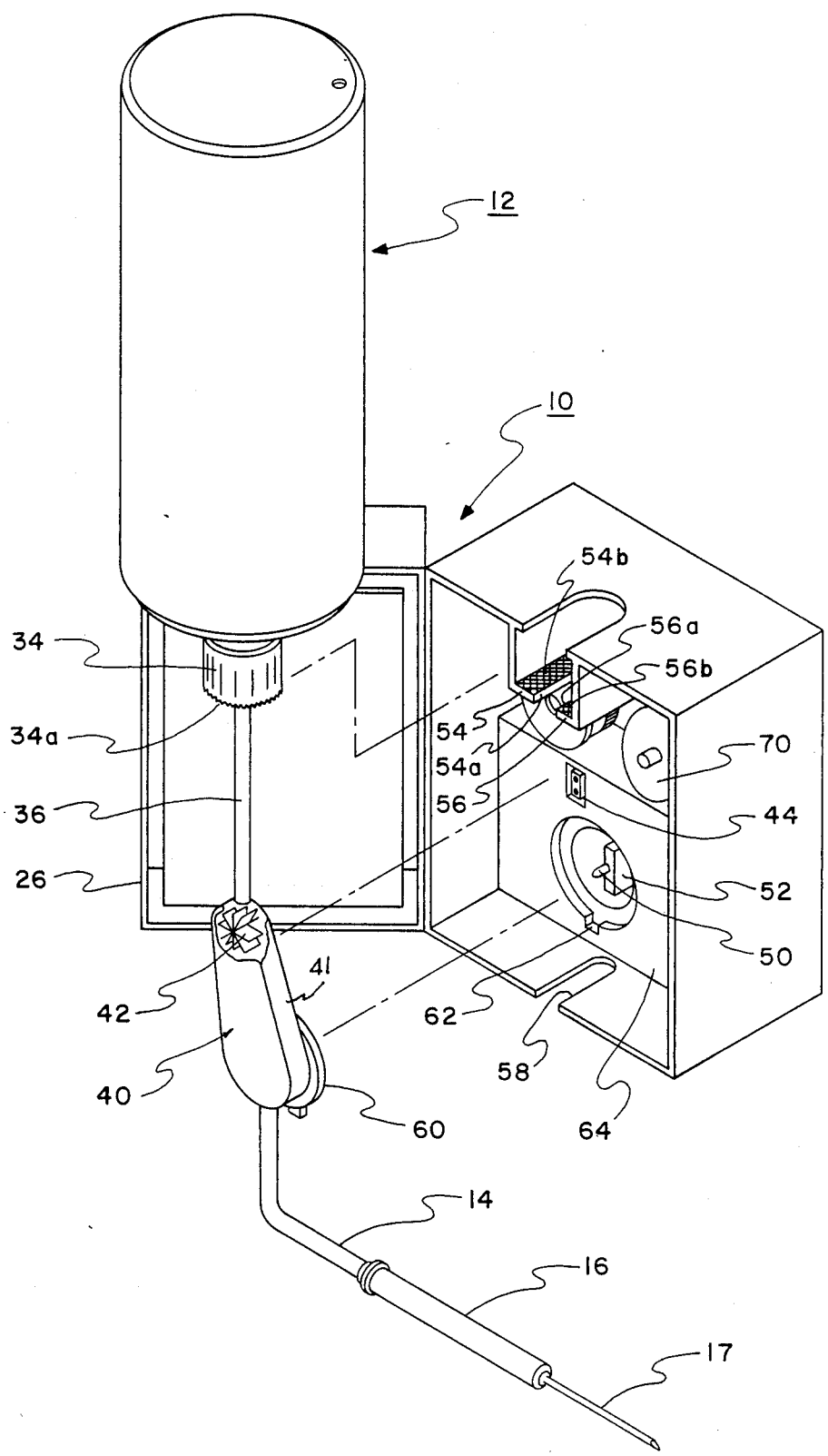
FIG. 5 is a front elevational view of the system shown in FIG. 1 with the control box open and the remainder of the system removed therefrom.

With particular reference to FIGS. 3 and 5 it may be seen that the transducer 40 includes a hermetically sealed housing 41 having a paddle or vane wheel 42 rotatably mounted directly below the fluid inlet to the transducer so that the angular velocity of the wheel 42 is proportional to the rate of fluid flow through the transducer.

An optical sensor 44 mounted in the box 10 adjacent to the vanes senses the speed of rotation of the wheel 42 through a transparent window 46 at the rear of the transducer 40 as shown in FIG. 3 and transmits to the microprocessor a train of electric pulses at a frequency proportional to the rate of fluid flow past the wheel 42.

The transducer 40 also includes a circular diaphragm 48 which engages the rounded end of an actuator button 50 extending from a linear potentiometer 52 mounted to the rear wall of the control box. The potentiometer produces an analog signal having an amplitude proportional to the distance the button 50 is pressed into the potentiometer 52. The button is spring biased into its fully projected position as shown in FIG. 5 and engages the diaphragm 48 when the door 26 is closed. It will thus be seen that the output of the potentiometer is a signal proportional to the fluid pressure acting on the inner face of the diaphragm 48.

The container 12 including the reservoir 30 and the valve 32, the tube 36, the transducer 40, the tube 14 and the cannula 16 are fixedly connected together and are supplied as a unit in a sterile condition with the reservoir containing a predetermined volume of a particular I.V. fluid at a predetermined elevated pressure.

When the system is to be used the door 26 is opened and the container 12 is positioned above the top wall of the control box 10 with the cap located on a pair of rails 54 and 56 and the upper tube 36 freely extending down through the slot located between the edges 54A and 56A of the rails 54 and 56.

The lower tube 14 extends through a slot 58 in the bottom wall of the box 10. A generally circular keyed portion 60 of the housing of the transducer 40 fits into a complementary opening 62 in the front wall of compartment 64 in the control box 10 to accurately position the transducer 40 to align the wheel 42 with the optical sensor 44.

Mounted below the rails 54 and 56 and on opposite sides of the slot between the rails is a mechanism for controlling the flow of fluid through the system. More particularly, a pair of cooperating wheels or discs 68 and 70 are respectively mounted for rotation on mutually parallel axes with the tube 36 passing between the rims of the discs. The disc 70 has a generally cylindrical rim 70A while the disc 68 has an eccentric rim 68A as best shown in FIG. 3.

Figure 4:
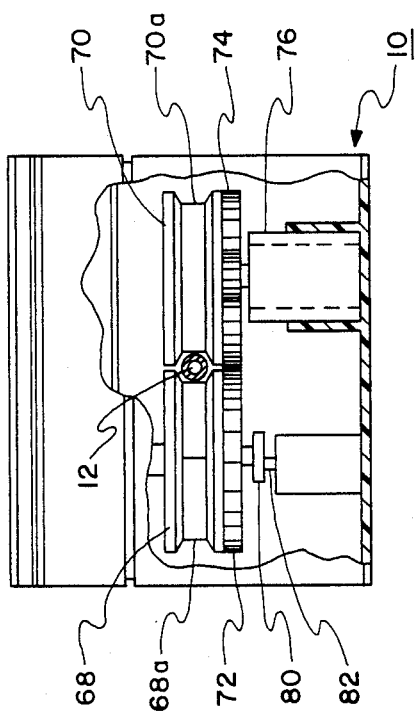
FIG. 4 is a partially sectioned view taken along the line 4—4 in FIG. 3.

The disc 68 and the disc 70 are respectively provided with mating spur gears 72 and 74, and an electric servo motor 76 drives the discs 68 and 70 through a drive gear 78. The rotor of the motor 76 is under the control of and is thus positioned by the microprocessor and positions the discs 68 and 70 at an angle between that angular position wherein the tube 12 is completely compressed and thus closed by the rims of the discs 68 and 70 and a fully open position as shown in FIG. 4.

In order to facilitate insertion of the tube 36 between the rims of the discs 68 and 70, the disc 68 is rotatably mounted to a crank arm 80 which is pivotably mounted to a shaft 82 for movement of the disc into the open position shown in phantom in FIG. 3 wherein the rim of the discs 68 and 70 are widely spaced apart. A conventional snap lock (not shown) holds the disc in the operative position (solid lines) when the door 26 is closed.

Figure 6:
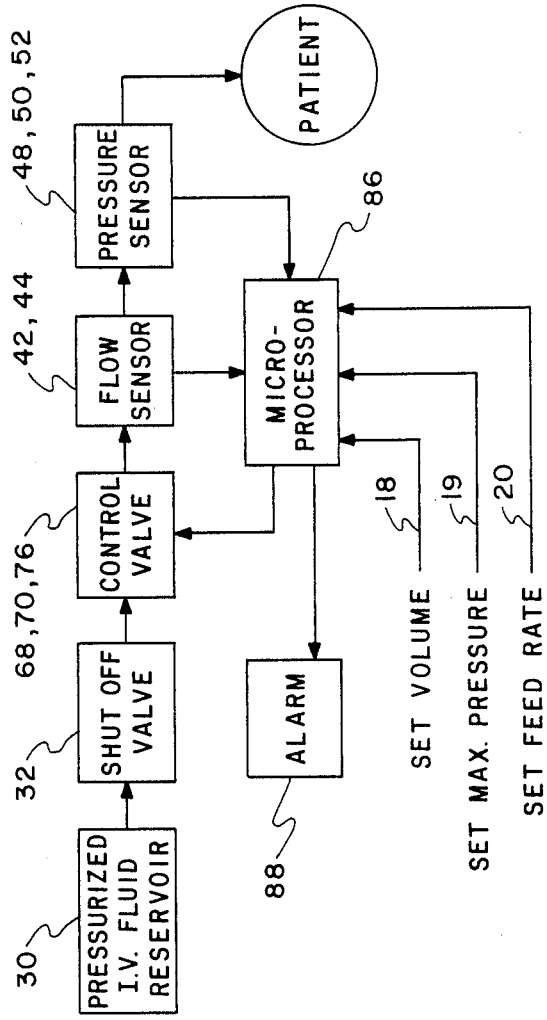
FIG. 6 is a block diagram of the system shown in FIG. 1.

Referring now to FIG. 6 there is shown the system of the present invention in schematic form. As may be seen, the output of the pressurized I.V. fluid reservoir 30 is coupled through the shut off valve 32 to the control valve made up of the disc 68 and 70 and the syncro motor 76. The position of this control valve is under the control of a micro processor 86. The output of the control valve is supplied to a flow sensor comprising the wheel 42 and the optical sensor 44 by the tube 36 and the output from that sensor flows through the pressure sensor comprising the diaphragm 48, the actuator button 50 and the transducer 52 to the patient in which the needle 17 is inserted. The variable output signals from the flow sensor and from the pressure sensor are supplied to the microprocessor 86 which is also supplied with the preset signals from the set volume input 18, the set maximum pressure input 19 and the set feed rate 20 from the control buttons at the front of the control box. An alarm device 88 which is preferably both visual and audible is also controlled by an output from the microprocessor 86.

Figure 2:
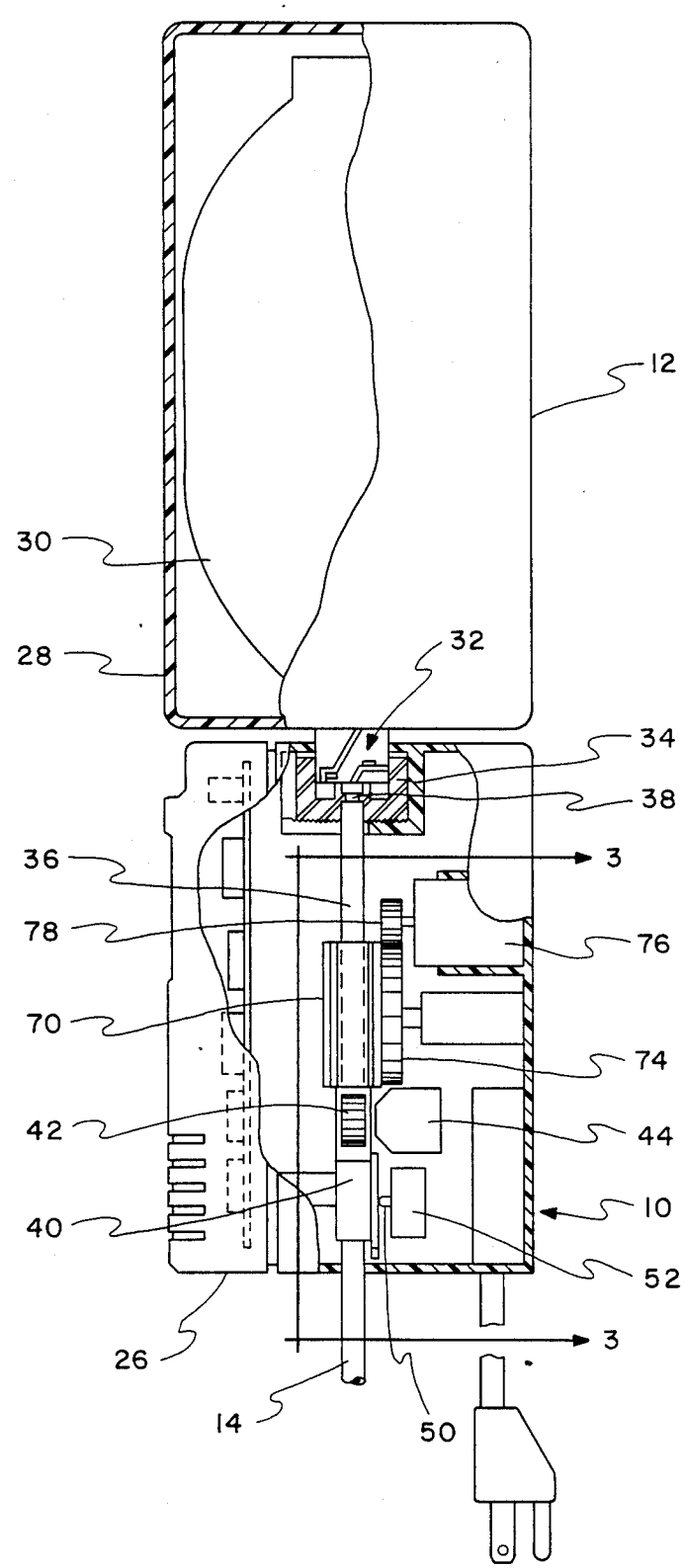
FIG. 2 is a view similar to FIG. 1 wherein the parts of the system are partially sectioned to show the operative portions thereof.

In operation, the door 26 of the control box is opened and the I.V. fluid container 12 together with the parts connected thereto is inserted into the control box as shown in FIGS. 2 and 5. It may be seen from FIG. 5 that the annular surface at the bottom of the cap 34 is provided with radial grooves 34A which mate with longitudinal grooves 54B and 56B on the top surfaces of the rails 54 and 56. With the circular portion 60 of the transducer inserted into the complementary opening 62 in the control box the door 26 is then closed. As heretofore explained, the push buttons 18, 19 and 20 are then actuated to enter into the microprocessor the volume of I.V. fluid to be supplied to the patient, the maximum pressure at which that fluid should be applied and the feed rate at which it is to be applied. These numbers are all prescribed by the attending physician. With the system in the off condition the microprocessor 86 positions the rotor of the motor 76 to cause the discs 68 and 70 to be rotated to that position wherein the tube 36 is completely closed. When the system is to be used the operator then rotates the container 12 relative to the box which holds the cap 34 in a fixed position whereby rotation of the container 12 through 90 degrees fully opens the valve 32. Preferably the valve 32 is an on-off valve which is either fully open when in one indexed position or fully closed when in the other indexed position. There is no need for use of this valve to adjust the flow rate in this system and the elimination of a variable rate control valve on the reservoir itself reduces the chance of error in the operation of the system which is fully automatic and requires that the fluid pressure of the fluid leaving the reservoir be above a predetermined pressure.

If the rate of flow of the fluid through the flow sensor is less than the set feed rate the microprocessor operates the motor 76 to rotate the discs 68 and 70 to a position wherein the cross sectional area of the portion of the tube between the rims of the discs 68 and 70 is increased whereby the flow rate increases until it matches the set feed rate and further rotation of the discs 68 and 70 is terminated. The signal from the flow sensor is integrated in the microprocessor 86 to provide a signal which is compared to the set volume signal. When these two signals are equal the microprocessor then operates the motor 76 to rotate the discs 68 and 70 to the fully closed position wherein the flow of fluid through the system is interrupted. If at the time the reservoir contains fluid under pressure then the container 12 should be rotated to close the shut off valve 32 before opening the door 26 and removing the system from the control box. As a protective measure, since the fluid reservoir is pressurized to a pressure substantially greater than should be applied to the patient the pressure sensor is provided in the line between the flow sensor and the patient. The output signal from the pressure sensor is compared in the microprocessor with the maximum pressure which was set therein by the set maximum pressure button 19, and if that pressure exceeds the set maximum pressure then the microprocessor immediately operates the motor 76 to rotate the disc 68 and 70 to the fully closed position and actuates the alarm 88. The attendant then determines what the problem is and corrects it.

Figure 7:
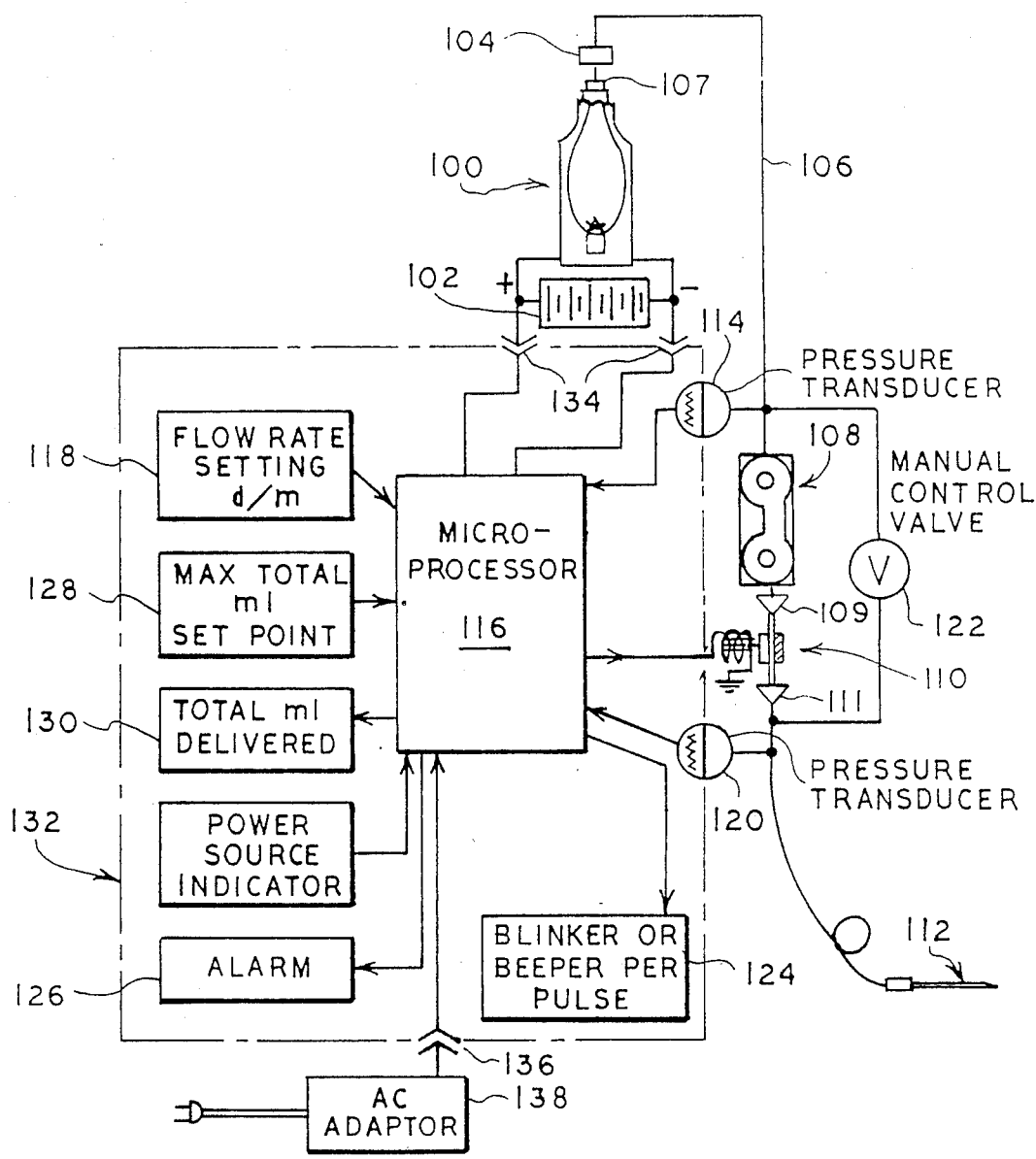
FIG. 7 is schematic diagram of an IV control system constituting another embodiment of the invention.

Referring to FIG. 7, a reservoir 100 for holding a supply of intravenous fluid may be self pressurized and constructed like the reservoir 12 described hereinabove, or if desired, the IV fluid in the reservoir may be at ambient pressure and supplied to the patient under the force of gravity. Preferably the reservoir unit includes a battery 102 physically packaged thereto to enable the system to be completely portable for use in the field or wherever conventional power lines are not available.

A conventional quick-connect-disconnect 104 is used to connect a flexible tube 106 to the outlet port 107 from the reservoir 100. As shown, the outlet port 107 is at the top, wherefore in this particular embodiment the reservoir must be of the pressurized type. As may be seen, the line 106 connects to the inlet of a flow resistor 108 which is preferably of the type described in U.S. Pat. No. 3,323,550. The flow resistor 108 is insensitive to changes in the viscosity and pressure of the fluid and is used in this system to provide a constant time delay for the fluid passing therethrough.

The outlet from the flow resistor 108 is connected via a check valve 109 to the inlet port of a solenoid operated, peristaltic pump and control valve 110. The outlet port of the valve 110 is connected via a check valve 111 to the inlet of a cannula 112 which is adapted to be inserted into the patient for delivery of the IV solution thereto.

A first pressure responsive transducer 114 is coupled to the line 106 upstream of the flow resistor 108 to develop an electric signal proportional to the pressure upstream of the valve 110. This signal is coupled to an input of a microprocessor 116 which controls the valve 110 to maintain the IV flow rate at the preset value entered into the microprocessor via an input 118. At the present time the IV flow rate is manually entered into the microprocessor, but it will be understood that other means, such for example as an optical reader can be used for this purpose.

A second pressure responsive transducer 120 is coupled to the IV line downstream of the flow control valve 110 and it produces an electric signal proportional to the pressure in the line downstream of the flow control valve 110. The output signal from the transducer 120 is connected to another input of the microprocessor 116.

In order to permit use of the system in the event of a failure of the automatic flow rate control, a manually adjustable flow control valve 122 is connected between the inlet to the flow resistor 108 and the outlet of the flow control valve 110.

The microprocessor 116 generates a train of output pulses which causes the valve 110 to open and close at the rate of occurrence of these pulses. Thus the flow rate through the valve 110 is proportional to the frequency of the control pulses and the pressure differential across the valve. The microprocessor thus responds to the differential pressure as sensed by the two pressure transducers 114 and 120 to maintain precisely the preset flow-rate. Because of the two check valves 109 and 111, the valve 110 functions as a pump when the pre-valve pressure is about the same as or less than the post-valve pressure. Consequently, if the system is being gravity fed and the reservoir falls below the patient, fluid will still be infused into the patient.

A sensable signal, either audible or visual or both, is emitted by a device 124 to indicate to the operator that the system is functional and the IV solution is being fed to the patient.

Also, an alarm device 126 is incorporated into the control system and is activated by the microprocessor 116 when either or both of the transducers 114 and 120 sense an undesirable condition. In addition to the flow rate setting 118, a preset volume total 128 is provided and a digital readout 130 of the total volume of IV fluid delivered is provided. Moreover, if desired, a digital readout (not shown) of the actual flow rate can be provided.

As shown in FIG. 7 the electronic controls are located in an instrument housing 132. A set of input jacks 134 are provided for connecting the battery 102 to the system and a set of jacks 136 are provided for connecting the system to a public AC power line via an AC adapter or rectifier 138 when AC power is available.

Figure 8:
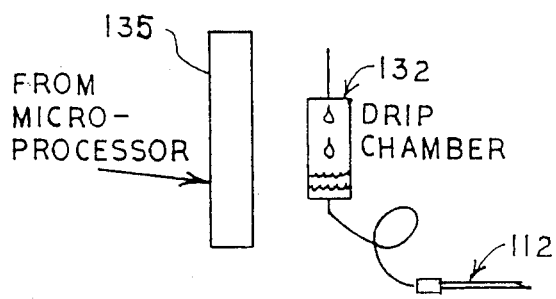
FIG. 8 shows a modification of the system of FIG. 7 to include a drip chamber.

In the embodiment of FIG. 8 the post valve pressure transducer is eliminated and a conventional drip chamber 132 is provided in the line. To facilitate reading of the drip chamber a back light 135 controlled by the microprocessor 116 is positioned in proximity to the drip chamber 132.

Figure 9:
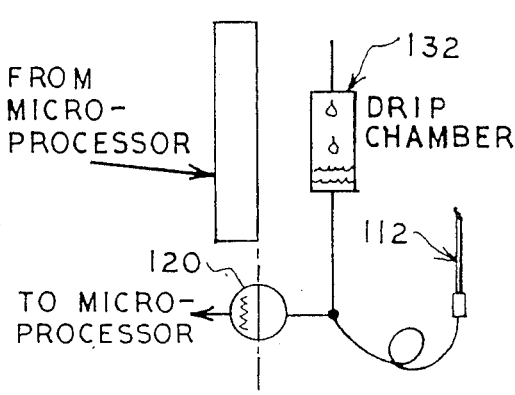
FIG. 9 shows a modification of the system of FIG. 8.

In the embodiment of FIG. 9 the drip chamber 132 is connected between the flow control valve 110 and the transducer 120 wherefore the transducer 120 produces a signal proportional to that of the fluid pressure at the cannula 112.

While the present invention has been described in connection with particular embodiments thereof, it will be understood by those in the art that many changes may be made without departing from the true spirit and scope of the present invention. Therefore, it is intended by the appended claims to cover all such changes and modifications which come within the true spirit and scope of this invention.

What is claimed:

1. Apparatus for supplying a fluid to a patient, comprising in combination
    a reservoir containing a quantity of said fluid,
    an outlet port from said reservoir,
    a cannula for insertion into said patient,
    conduit means connected between said outlet port and said cannula,
    flow control means connected in said conduit means for controlling the rate of flow of fluid through said conduit means,
    transducer means connected between said outlet port and said flow control means for outputting a first signal representative of the pressure in said conduit means upstream of said flow control means,
    means for outputting a second signal representative of a manually set flow rate,
    computer means responsive to said first and second signals for operating said flow-control means for maintaining the rate of flow of said fluid through said conduit at said manually set flow rate, and
    a drip chamber connected in said conduit means between said flow control means and said cannula.

2. Apparatus according to claim 1, comprising
    second transducer means connected between said flow control means and said cannula for outputting a third signal representative of the pressure in said said conduit means downstream of said flow control means, and
    said computer means being responsive to said first and third signals to generate an alarm signal when the pressure at said second transducer is not less than the pressure at said first mentioned transducer.

3. Apparatus according to claim 2 comprising
    a first check valve connected in said conduit between said outlet port and said flow control means, and
    a second check valve connected in said conduit between said flow control means and said cannula.

4. Apparatus according to claim 1 comprising
    flow resistance means connected in said conduit means between said transducer means and said flow control means for providing a constant resistance to the flow of said fluid to said flow control means.

5. Apparatus according to claim 4 wherein said reservoir comprises
    a container in which said fluid is maintained at a pressure greater than ambient pressure.

6. Apparatus according to claim 5, comprising
    second transducer means connected between said flow control means and said cannula for outputting a third signal representative of the pressure in said conduit means downstream of said flow control means,
    said computer means being responsive to said first and third signals to generate an alarm signal when the pressure at said second transducer is not less than the pressure at said first mentioned transducer.

7. Apparatus according to claim 4 comprising
    second transducer means connected between said flow control means and said cannula for outputting a third signal representative of the pressure in said conduit means downstream of said flow control means,
    said computer means being responsive to said first and third signals to generate an alarm signal when the pressure at said second transducer is not less than the pressure at said first mentioned transducer and,
    means connecting said third signal to said computer means.

* * * * *